US011498742B2

(12) United States Patent
Clarke et al.

(10) Patent No.: US 11,498,742 B2
(45) Date of Patent: Nov. 15, 2022

(54) TECHNIQUES AND PACKAGES FOR PACKAGING MEDICAL SUPPLIES

(71) Applicant: Medtronic Vascular, Inc., Santa Rosa, CA (US)

(72) Inventors: David Clarke, Galway (IE); Joshua Hillas, Galway (IE)

(73) Assignee: Medtronic Vascular, Inc., Santa Rosa, CA (US)

( * ) Notice: Subject to any disclaimer, the term of this patent is extended or adjusted under 35 U.S.C. 154(b) by 449 days.

(21) Appl. No.: 16/529,120

(22) Filed: Aug. 1, 2019

(65) Prior Publication Data

US 2020/0047974 A1 Feb. 13, 2020

Related U.S. Application Data

(60) Provisional application No. 62/716,556, filed on Aug. 9, 2018.

(51) Int. Cl.
*B65D 81/26* (2006.01)
*B65B 5/04* (2006.01)
(Continued)

(52) U.S. Cl.
CPC .............. *B65D 81/268* (2013.01); *B65B 5/04* (2013.01); *B65B 55/10* (2013.01); *B65D 75/30* (2013.01); *B65D 75/522* (2013.01)

(58) Field of Classification Search
CPC .... B65D 75/30; B65D 75/522; B65D 81/264; B65D 81/267; B65D 81/268
(Continued)

(56) References Cited

U.S. PATENT DOCUMENTS

| 3,552,638 | A |   | 1/1971 | Quackenbush |
| 3,685,720 | A | * | 8/1972 | Brady ................... B65D 75/66 |
| | | | | 206/439 |

(Continued)

FOREIGN PATENT DOCUMENTS

| CN | 107001873 A | 8/2017 |
| DE | 19 41 545 A1 | 7/1970 |

(Continued)

OTHER PUBLICATIONS

PCT/US2019-044679, The International Search Report and the Written Opinion of the International Searching Authority.
(Continued)

*Primary Examiner* — Luan K Bui
(74) *Attorney, Agent, or Firm* — Medler Ferro Woodhouse & Mills PLLC (57) ABSTRACT

In some examples, a package includes a package body enclosing a medical supply. The package body defines a window. The package includes a breathable membrane adjacent the package body and extending across the window. The package includes a moisture oxygen scavenger adjacent the package body and extending across the breathable membrane. The package includes an adhesive layer configured to hold the moisture oxygen scavenger adjacent the breathable membrane. In some examples, a technique includes sterilizing a package precursor including the package body and the breathable membrane, and after the sterilizing, adhering the moisture oxygen scavenger to the package body to form the package.

18 Claims, 5 Drawing Sheets

(51) Int. Cl.
    *B65B 55/10* (2006.01)
    *B65D 75/30* (2006.01)
    *B65D 75/52* (2006.01)

(58) Field of Classification Search
    USPC .......................... 206/204, 363–370, 438–439
    See application file for complete search history.

(56) References Cited

U.S. PATENT DOCUMENTS

| | | | |
|---|---|---|---|
| 3,991,881 A | 11/1976 | Augurt | |
| 4,270,658 A | 6/1981 | Schuster | |
| 4,407,874 A | 10/1983 | Gehrke | |
| 4,660,721 A | 4/1987 | Mykleby | |
| 5,551,781 A * | 9/1996 | Wilkes | B65D 27/28 |
| | | | 206/439 |
| 5,653,090 A | 8/1997 | Weiss et al. | |
| 5,816,709 A * | 10/1998 | Demus | B65D 33/24 |
| | | | 383/88 |
| 5,947,287 A | 9/1999 | Weiss et al. | |
| 6,251,489 B1 | 6/2001 | Weiss et al. | |
| 7,296,678 B2 * | 11/2007 | Raynal-Olive | B65B 55/10 |
| | | | 422/26 |
| 9,033,152 B2 * | 5/2015 | Ludvig | A61L 2/00 |
| | | | 206/439 |
| 10,351,305 B2 * | 7/2019 | Dworak | B65B 7/02 |
| 2005/0103666 A1 * | 5/2005 | Grimard | A61L 2/183 |
| | | | 206/438 |
| 2005/0268573 A1 | 12/2005 | Yan | |
| 2006/0054523 A1 * | 3/2006 | Porret | A61L 2/206 |
| | | | 206/439 |
| 2009/0314676 A1 * | 12/2009 | Peck | B65D 33/01 |
| | | | 206/438 |
| 2012/0181193 A1 | 7/2012 | Wu | |
| 2014/0133785 A1 | 5/2014 | Diviesti et al. | |

FOREIGN PATENT DOCUMENTS

| | | |
|---|---|---|
| DE | 42 29 314 A1 | 3/1994 |
| EP | 0 306 207 A1 | 3/1989 |
| WO | 96/39340 A1 | 12/1996 |
| WO | 20050073091 A2 | 8/2005 |
| WO | 2015130608 A1 | 9/2015 |
| WO | 20160069864 A2 | 5/2016 |
| WO | 2016100153 A2 | 6/2016 |

OTHER PUBLICATIONS

China Intellectual Property Administration, First Office Action, China Application No. 201980059084.7, dated Jul. 14, 2022, 8 pages.

* cited by examiner

TECHNIQUES AND PACKAGES FOR PACKAGING MEDICAL SUPPLIES

CROSS-REFERENCE TO RELATED APPLICATIONS

The present application claims the benefit of the filing date of U.S. provisional application No. 62/716,556, filed Aug. 9, 2018, the contents of which are incorporated by reference herein in their entirety.

TECHNICAL FIELD

The present disclosure relates to, in some examples, packages for medical supplies.

BACKGROUND

Packages may be used to house medical supplies in a sterile environment. In addition to helping to protect the medical supplies from damage that may be caused by handling or storage, packages may help preserve the sterility of medical supplies up to the time of use. For example, a package may house a medical device or another medical supply within a sealed space, and the medical package, including the medical device or other medical supply, may be sterilized prior to distribution. Thus, the package may maintain the sterility of medical supplies within a sealed environment prior to use of the medical device or other medical supply. At the time of use, a clinician may retrieve the medical device or other medical supply from the package by opening the container in a sterile environment to help preserve the sterility of the medical supplies.

SUMMARY

The present disclosure describes example devices, systems, and techniques for packaging medical products.

In some examples, a package includes a package body enclosing a medical supply. The package body defines a window. The package includes a breathable membrane adjacent the package body and extending across the window. The package includes a moisture oxygen scavenger adjacent the package body and extending across the breathable membrane. The package includes an adhesive layer configured to hold the moisture oxygen scavenger adjacent the breathable membrane.

In some examples, a technique includes sterilizing a package precursor. The package precursor includes a package body enclosing a medical supply. The package body defines a window. The package precursor includes a breathable membrane adjacent the package body and extending across the window. The technique includes, after the sterilizing, adhering a moisture oxygen scavenger extending across the breathable membrane to the package body to form a package.

The details of one or more aspects of the disclosure are set forth in the accompanying drawings and the description below. Other features, objects, and advantages of the techniques described in this disclosure will be apparent from the description and drawings, and from the claims.

BRIEF DESCRIPTION OF THE DRAWINGS

Reference is made to the attached drawings, wherein elements having the same reference numeral designations represent similar elements throughout.

DETAILED DESCRIPTION

Packages may be used to house and protect one or more medical supplies before use. In addition to maintaining sterility and integrity, packages may protect medical supplies from one or both of moisture or oxygen. In some examples, a package may define a window to facilitate sterilization, for example, by allowing a sterilizing agent to enter the package through the window during sterilization, after the package is otherwise sealed around the medical supply. A breathable membrane may be disposed across the window to permit the sterilizing agent to enter the package through the window, while acting as a barrier to contaminants, such as microorganisms, liquids, and/or solids. However, the breathable membrane may allow moisture vapor, oxygen, or other agents to enter the package after sterilization. To prevent or reduce such exposure of the medical supply to moisture or oxygen, the package may include a moisture oxygen scavenger. By including such a configuration, a package may allow a medical supply to be placed in the package, the package sealed, sterilized by introducing a sterilizing agent into the package through the breathable membrane, then the breathable membrane covered with the moisture oxygen scavenger to substantially fully seal the package.

In some examples, the moisture oxygen scavenger may be in the form of a layer or a sachet, and thus have a relatively low profile and substantially conform to a package body of the package. One or both of the adhesive layer or the low profile may promote retention of the moisture oxygen scavenger on the package body by reducing or preventing inadvertent removal in response to external forces. In this way, the moisture oxygen scavenger may draw out or divert moisture and oxygen from entering the internal volume of the package, or substantially absorb and retain moisture or oxygen before the moisture or oxygen enters the internal volume of the package.

Figure 1A:
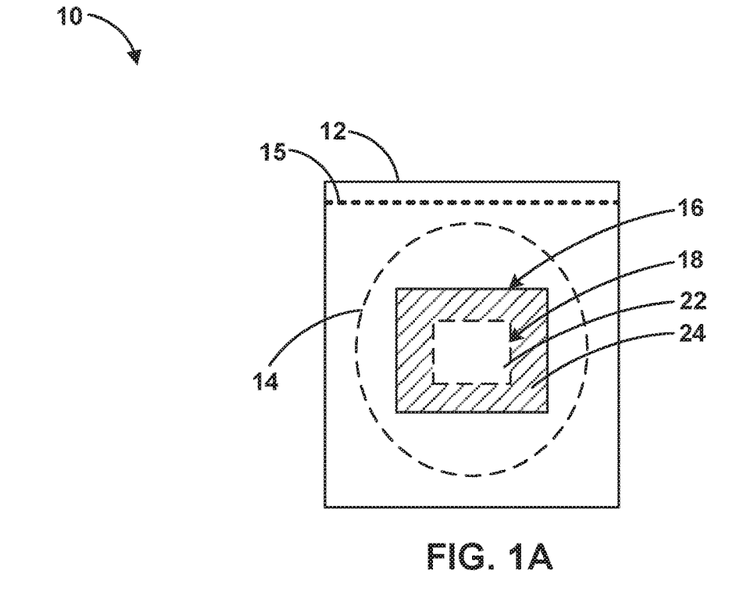
FIG. 1A is a conceptual diagram illustrating a top view of an example package including a package body enclosing a medical supply with a moisture oxygen scavenger extending across a breathable member adjacent the package body.
Figure 1B:
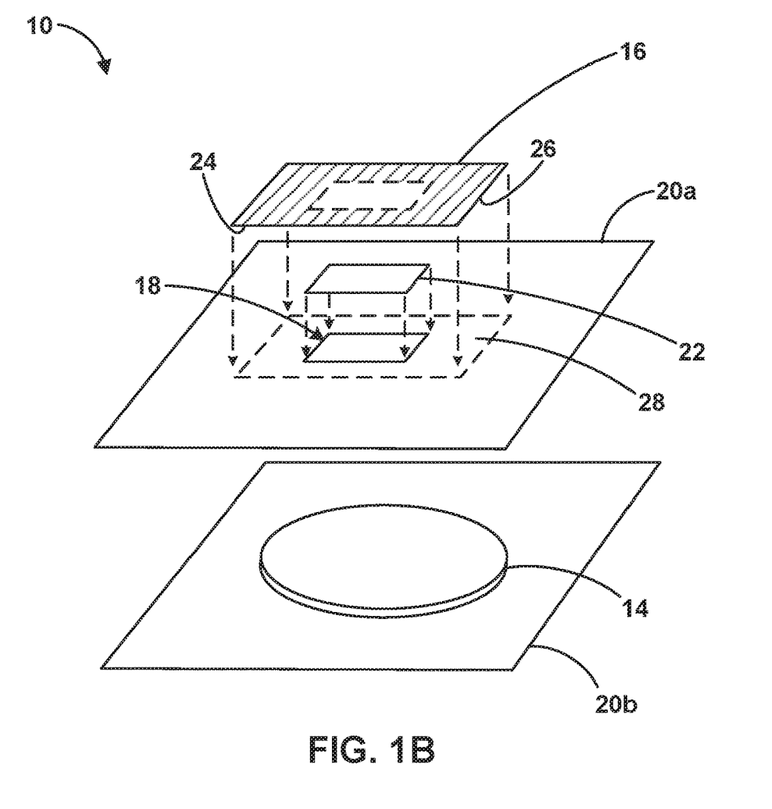
FIG. 1B is a conceptual diagram illustrating an exploded view of the package of FIG. 1A.

FIG. 1A is a conceptual diagram illustrating a top view of an example package 10 including a package body 12 enclosing a medical supply 14 with a moisture oxygen scavenger 16 extending across a breathable member 22 adjacent package body 12. FIG. 1B is a conceptual diagram illustrating an exploded view of package 10 of FIG. 1A.

Package body 12 is configured to receive and house medical supply 14. In some examples, package body 12 may be defined by one, two, or more package body portions. For example, as shown in FIG. 1B, package body 12 may include a first package body portion 20a and a second package body portion 20b. In some examples, one or both of first package body portion 20a or second package body portion 20b include a panel. For example, package body 12 may define a pouch, and first and second package body portions 20a and 20b may define panels of the pouch. In some examples, first and second package body portions 20a and 20b may be joined or sealed to each other at one or more peripheral regions or edges. In some examples, first and second package body portions 20a and 20b are sealed at three respective edge regions, to define a pouch with an opening defined by the fourth respective edge regions. Medical supply 14 may be introduced into package body 12 through the opening. After medical supply 14 is introduced into package body 12, package body 12 may be sealed by providing a seal 15 along or adjacent the opening. In some examples, seal 15 is a thermal seal formed by thermally bonding first and second package body portions 20a and 20b adjacent seal 15. In some examples, first and second package body portions 20a and 20b may have a substantially symmetric geometrical configuration relative to each other, as shown in FIG. 1B. While first and second package body portions 20a and 20b are shown as discrete or separate in example package 10 of FIGS. 1A and 1B, in other examples, first and second package body portions 20a and 20b may be different portions of a continuous, unitary, or integrated package. For example, first and second package body portions 20a and 20b may be foldable regions of a continuous sheet, web, or panel.

In some examples, one or more portions of package body 12, for example, first and second package body portions 20a and 20b, may be flexible, such that package 10 is relatively flexible and conformable to medical supply 14. In other examples, one or more portions of package body 12 is relatively rigid (e.g., self-supporting). Further, in these examples, one or more portions of package body 12 may provide structural stability and support to medical supply 14. In yet other examples, a first section of package body 12 may be more flexible than another section of package body 12. One or more sections of package body 12 may include one or more of a woven panel, a non-woven panel, a plastic panel, a polymer film, a paper film, a coated paper film, a metalized polymer film, a foil, a tray, a thermoform, a two-piece clamshell, or a folded clamshell. In some examples, package body 12 may be substantially impervious to one or more of gas, moisture, vapor, fluids, particulates, microorganism, or contaminants, except for predefined regions (for example, windows for sterilization) as described in the disclosure.

Package 10 may be sterilized after medical supply 14 is introduced into package body 12. In some examples, package 10 may be sterilized by exposing package body 12, an internal volume of package 10, and medical supply 14 in package 10, to a sterilizing agent. For example, the sterilizing agent may include a gaseous or vapor composition include one or more of a gas, an aerosolized component, a suspended component, droplets, or the like. In some examples, the sterilizing agent includes ethylene oxide gas.

To facilitate passage of such a gaseous or vapor composition into the internal volume of package 10 for sterilization, package 10 may define at least one window 18. Window 18 may be polygonal, for example, rectangular as shown in FIGS. 1A and 1B, or may be in the form of any closed simple, compound, or piecewise curved or linear contour. For example, window 18 may include a circle or circular arcs, an ellipsoid or an ellipsoidal arc, or any suitable combination of linear and curved contours. In some examples, window 18 may include a plurality of openings or pores. The plurality of openings or pores may be arranged along any predetermined contour or in any predetermined two-dimensional arrangement, for example, a grid or an array.

To permit entry of the sterilizing agent into the internal volume of package 10, while preventing the entry of contaminants, package 10 includes breathable membrane 22 adjacent window 18. For example, breathable membrane 22 may extend substantially across window 18 or otherwise cover window 18. In some examples, breathable membrane 22 may have substantially the same size and contour as window 18, and closely align with window 18. In other examples, breathable membrane 22 may have a shape or contour different from that of window 18, but sufficiently large to substantially cover window 18. Breathable membrane 22 may be polygonal, for example, rectangular as shown in FIGS. 1A and 1B, or may be in the form of any closed simple, compound, or piecewise curved or linear contour. For example, breathable membrane 22 may include a circle or circular arcs, an ellipsoid or an ellipsoidal arc, or any suitable combination of linear and curved contours. Breathable membrane 22 may include more than one panel or membranes. In examples in which window 18 includes a plurality of openings or pores, breathable membrane 22 may be unitary and extend across all openings or pores, or may include a plurality of membranes or portions respectively extending across or covering one or more openings or pores.

Breathable membrane 22 may include a woven or nonwoven material. For example, breathable membrane 22 may include one or more of polymeric, glass, ceramic, cellulosic, or biological fibers or yarn. In some examples, breathable membrane 22 includes a spunbonded olefin sheet product, such as Tyvek® (DuPont USA, Wilmington, Del.), a synthetic fiber-based substrate, such as Ovantex® (Oliver Healthcare Packaging, Grand Rapids, Mich.), or a fabric including other polymers, for example, polyethylene, or nylon, or breathable paper. In some examples, breathable membrane 22 is gas- and/or moisture-permeable and microorganism- and/or liquid-impermeable. In some examples, a peripheral region of breathable membrane 22 may surround window 18. For example, the peripheral region of breathable membrane 22 may be at an exterior or an interior surface of package body 12 adjacent window 18. Breathable membrane 22 may be secured to or adhered to package body 12 adjacent window 18 by thermal bonding or welding, an adhesive, or any other suitable technique.

Moisture oxygen scavenger 16 includes a moisture oxygen scavenger composition. In some examples, the moisture oxygen scavenger composition is contained in a sachet, as described with reference to FIGS. 4A to 4D of the disclosure. In other examples, moisture oxygen scavenger 16 may include a carrier layer on which the moisture oxygen scavenger composition is applied, adhered, or otherwise carried. The carrier layer may include a continuous, woven fabric, or nonwoven fabric backing, for example, a polymeric sheet or fabric. In some examples, the carrier layer is flexible or conformable to package body 12. In other examples, the carrier layer is rigid. The carrier layer may have a relatively low moisture vapor transmission rate. For example, the moisture vapor transmission rate (MVTR) of the carrier layer, or of moisture oxygen scavenger 16 as a whole, may be relatively low. In some examples, the MVTR may be sufficiently low to prevent exposure of medical supply 14 to moisture or oxygen beyond respective predetermined thresholds over a predetermined shelf life of medical supply 14.

The moisture oxygen scavenger composition may include one or more of a desiccant (for example, one or more of silica gel, zeolites, calcium chloride, calcium sulfate, activated charcoal, clays), an oxygen scavenger or absorber (for example, one or more of elemental iron, iron alloys, iron compounds, citrates, ascorbic acid, or enzymes), or the like. In addition to an active desiccant or oxygen scavenger, the moisture oxygen scavenger composition may also include an inactive carrier, for example, a gel, a paste, an adhesive, a resin, or a binder, to carry the active component(s) and retain the moisture oxygen scavenger composition in moisture oxygen scavenger 16. In some examples, moisture oxygen scavenger 16 includes an indicator for indicating the extent of saturation or residual capacity of moisture oxygen scavenger 16. In some examples, the indicator may change color, indicating that moisture oxygen scavenger 16 is saturated or otherwise incapable of further absorbing moisture or oxygen. In some such examples, in response to such an indication, package 10 may be discarded, or moisture oxygen scavenger 16 may be replaced or refreshed.

Moisture oxygen scavenger 16 may extend substantially across window 18 (or breathable membrane 22, or both) or otherwise cover window 18 (or breathable membrane 22, or both). In some examples, moisture oxygen scavenger 16 may have substantially the same size and contour as breathable membrane 22, and closely align with breathable membrane 22. In other examples, moisture oxygen scavenger 16 may have a shape or contour different from that of breathable membrane 22, but sufficient to substantially cover breathable membrane 22. Moisture oxygen scavenger 16 may be polygonal, for example, rectangular as shown in FIGS. 1A and 1B, or may be in the form of any closed simple, compound, or piecewise curved or linear contour. For example, moisture oxygen scavenger 16 may include a circle or circular arcs, an ellipsoid or an ellipsoidal arc, or any suitable combination of linear and curved contours. Moisture oxygen scavenger 16 may include multiple units or portions. In examples in which package 10 includes a plurality of breathable membranes 22, moisture oxygen scavenger 16 may be unitary and extend across all portions of breathable membranes 22, or may include a plurality of units or portions respectively extending across or covering one or more of breathable membranes 22.

Moisture oxygen scavenger 16 may be secured to or adhered to package body 12 adjacent window 18 and breathable membrane 22 by thermal bonding or welding, an adhesive, or any other suitable technique. In some examples, moisture oxygen scavenger 16 defines a major surface 24 on which an adhesive layer 26 is applied. In some examples, major surface 24 and adhesive layer 26 face package body 12. For example, adhesive layer 26 contacts major surface 24 defined by moisture oxygen scavenger 16, and adhesive layer 26 is between package body 12 and moisture oxygen scavenger 16.

Adhesive layer 26 is configured to hold moisture oxygen scavenger 16 adjacent breathable membrane 22 and window 18, for example, by bonding or adhering moisture oxygen scavenger 16 to a surface region 28 defined by package body 12, a surface region defined by breathable membrane 22, or both. In some examples, surface region 28 is defined by breathable membrane 22, such that adhesive layer 26 adheres moisture oxygen scavenger 16 to breathable membrane 22, which is itself secured to package body 12. In some examples, surface region 28 may be partially defined by breathable membrane 22 and partially defined by package body 12, such that adhesive layer 26 adheres moisture oxygen scavenger 16 to breathable membrane 22 and a surface of package body 12.

As shown in FIGS. 1A and 1B, in some examples, adhesive layer 26 may substantially surround window 18, and moisture oxygen scavenger 16 may be substantially free of adhesive. Thus, adhesive layer 26 may be absent in a region extending across window 18 or breathable membrane 22. In other examples, as described with reference to FIG. 4D, adhesive layer 26 may extend substantially across entirety of major surface 24 of moisture oxygen scavenger 16. Adhesive layer 26 may be applied on major surface 24 of moisture oxygen scavenger 16 as a continuous coating, as a discontinuous coating, or as a predetermined pattern, for example, a grid or array of adhesive patches or regions. In some examples, adhesive layer 26 may include a plurality of spaced adhesive regions, for example, surrounding window 18, or extending across window 18. In some examples, adhesive layer 26 may form a substantially continuous seal between moisture oxygen scavenger 16 and package body 12 to reduce or prevent transfer or migration of moisture or air across a region between moisture oxygen scavenger 16 and package body 12. For example, such a substantially continuous seal may ultimately reduce or prevent transfer or migration of moisture into the internal volume of package body 12 across a gap between major surface 24 and package body 12. In some examples, adhesive layer 26 may form a hermetic seal between moisture oxygen scavenger 16 and package body 12.

Adhesive layer 26 may include any suitable adhesive composition, for example, a liquid, solid, gel, paste, suspension, colloid, or emulsion. Adhesive layer 26 may include a natural or synthetic adhesive. The natural or synthetic adhesive may include an acrylic, a cyanoacrylate, a hot-melt adhesive, a rubber, a silicone, a polyurethane, an epoxy, a hydrocolloid, a biological adhesive, fibrin, or the like. In some examples, adhesive layer 26 includes a pressure sensitive adhesive or pressure activated adhesive. In some examples, adhesive layer 26 includes a curable composition, for example, a heat curable, photocurable, or energy curable composition. While in example package 10 shown in FIG. 1A adhesive layer 26 includes a single layer, in other examples, package 10 may include a two-part adhesive. For example, adhesive layer 26 may include a first part of a two-part adhesive, while region 28 may carry a second part of a two-part adhesive, and the two-part adhesive may cure and bond after adhesive layer 26 is brought into contact with region 28 on package body 12.

In some examples, adhesive layer 26 may include a moisture oxygen scavenger composition. For example, a moisture oxygen scavenger composition may be mixed with an adhesive composition, and the mixture may be applied to a carrier layer to form an example moisture oxygen scavenger. In some examples, package 10 may not include a separate moisture oxygen scavenger 16, and may include adhesive layer 26 including a moisture oxygen scavenger composition. In some such examples, adhesive layer 26 may include moisture oxygen scavenger composition in a matrix of adhesive layer 26 adjacent breathable membrane 22.

Figure 2:
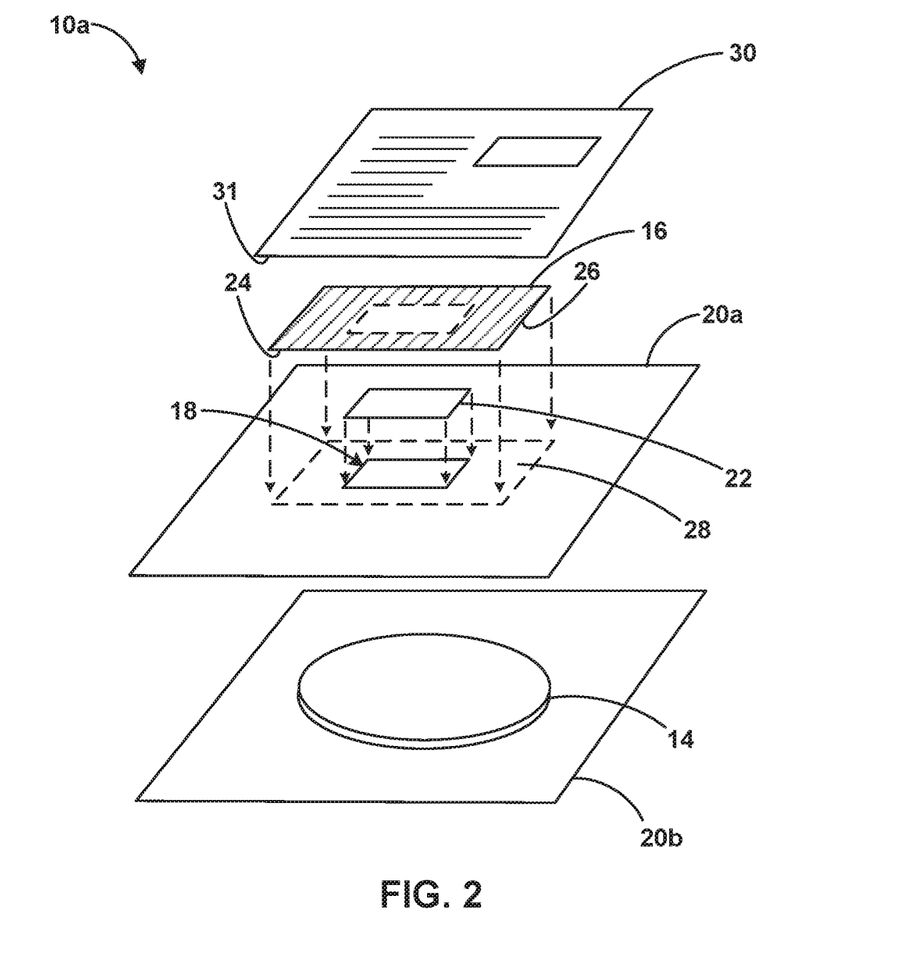
FIG. 2 is a conceptual diagram illustrating an exploded view of a package similar to the package of FIG. 1A, further including a backing layer adjacent the moisture oxygen scavenger, with adhesive applied to both the backing layer and the moisture oxygen scavenger.

FIG. 2 is a conceptual diagram illustrating an exploded view of a package 10a similar to package 10 of FIG. 1A, further including a backing layer 30 adjacent moisture oxygen scavenger 16, with adhesive applied to both backing layer 30 and moisture oxygen scavenger 16. For example, in addition to adhesive layer 26 applied to moisture oxygen scavenger 16, package 10a includes a second adhesive layer applied to a major surface 31 defined by backing layer 30. Major surface 31 may face package body 12, and the second adhesive layer may be between backing layer 30 and package body 12. In some examples, adhesive layer 26 may continuously extend past major surface 24 of moisture oxygen scavenger 16 across to major surface 31 of backing layer 30. The second adhesive layer on major surface 31 may be substantially similar in geometry and composition to that of adhesive layer 26. In some examples, the second adhesive layer may extend substantially across major surface 31 of backing layer 30, and may completely cover moisture oxygen scavenger 16. In some examples, backing layer 30 defines a product label. For example, one or more written and visual indicia, symbols, photographs, illustrations, letters, or numbers may be printed, embossed, engraved, or otherwise present on backing layer 30.

Backing layer 30 may include a sheet or panel of continuous material, porous material, or a woven or nonwoven fabric. In some examples, backing layer 30 includes one or more of a woven panel, a non-woven panel, a polymeric panel, a polymer film, polymeric fibers, paper, cellulosic fibers, film, a coated paper film, a metalized polymer film, or a foil. In some examples, backing layer 30 is substantially impervious to moisture, and acts as a secondary moisture barrier in addition to moisture oxygen scavenger 16.

Figure 3:
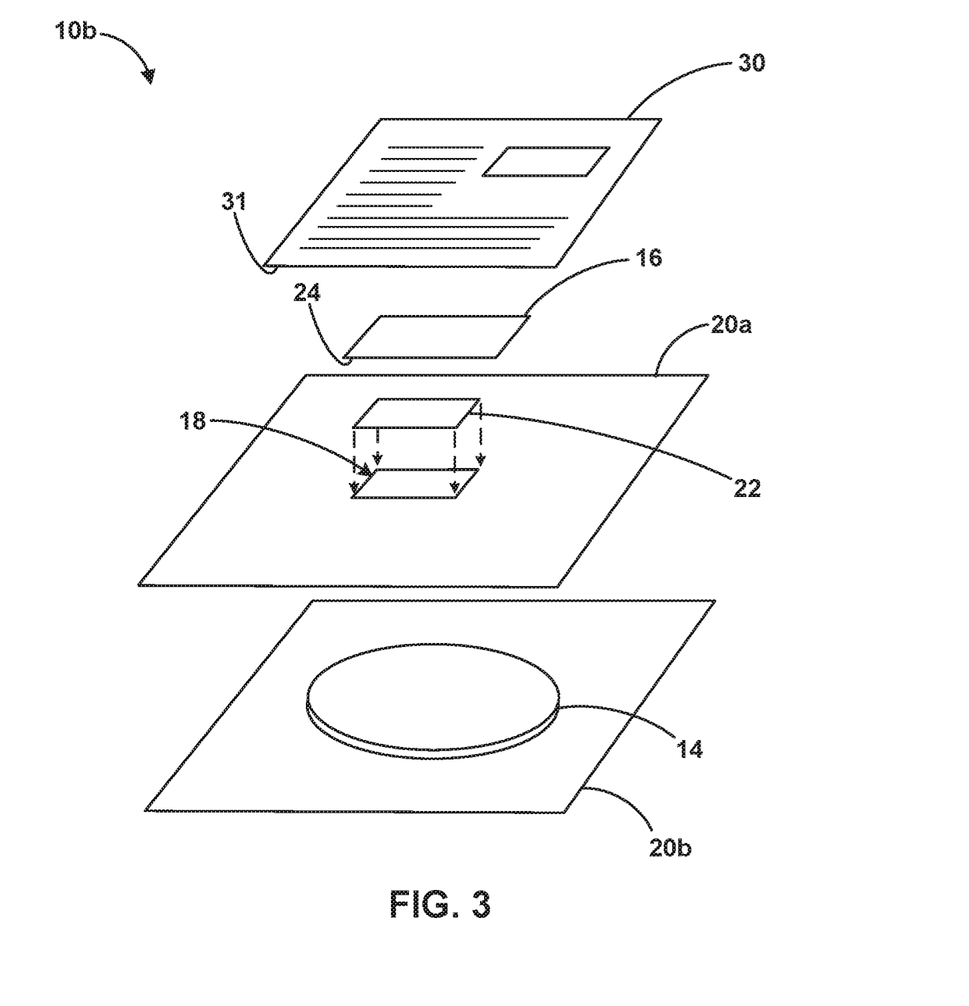
FIG. 3 is a conceptual diagram illustrating an exploded view of a package similar to the package of FIG. 1A, further including a backing layer adjacent the moisture oxygen scavenger, with adhesive applied to the backing layer.

FIG. 3 is a conceptual diagram illustrating an exploded view of a package 10b similar to package 10 of FIG. 1A, further including backing layer 30 adjacent moisture oxygen scavenger 16, with adhesive applied to backing layer 30. Unlike example package 10a described with reference to FIG. 2, in package 10b, adhesive layer 26 is absent, at least in a region adjacent moisture oxygen scavenger 16. Instead, adhesive may be applied only to major surface 31 of backing layer 30. For example, the adhesive may extend across entire major surface 31 of backing layer 30, to secure backing layer 30 against package body 12, with moisture oxygen scavenger 16 held between backing layer 30 and package body 12. In some examples, the adhesive may surround moisture oxygen scavenger 16, and may secure backing layer 30 against package body 12, with moisture oxygen scavenger 16 held between backing layer 30 and package body 12. The geometry and composition of the adhesive on backing layer 30 may be substantially similar to that described with reference to adhesive layer 26.

While moisture oxygen scavenger 16 may be a layer or substantially in the form of a layer, in other examples, moisture oxygen scavenger 16 is in the form of a sachet (or pouch, or package).

Figure 4A:
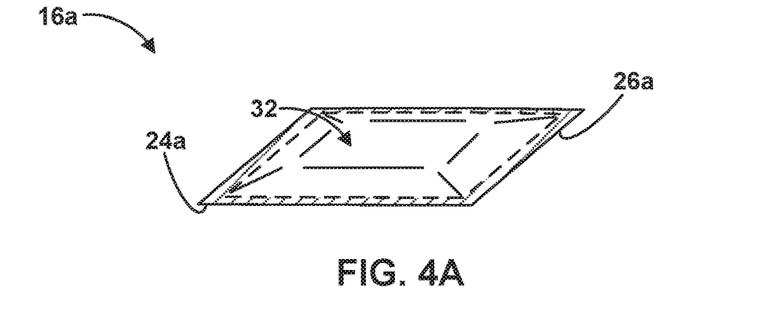
FIG. 4A is a conceptual diagram illustrating an example moisture oxygen scavenger including a sachet including a moisture oxygen scavenging composition.
Figure 4B:
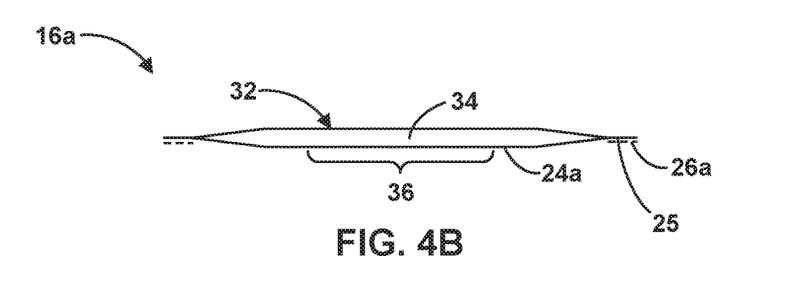
FIG. 4B is a conceptual diagram illustrating a side view of the sachet of FIG. 4A, with an adhesive layer applied to a peripheral surface region of the sachet.

FIG. 4A is a conceptual diagram illustrating an example moisture oxygen scavenger 16a including a sachet 32 including a moisture oxygen scavenging composition 34. FIG. 4B is a conceptual diagram illustrating a side view of sachet 32 of FIG. 4A, with adhesive layer 26a applied to a peripheral surface region 25 of sachet 32. Moisture oxygen scavenger 16 may be substituted or augmented with moisture oxygen scavenger 16a, for example, in package 10, 10a, or 10b. Moisture oxygen scavenging composition 34 may be substantially similar to the composition described with reference to moisture oxygen scavenger 16. Sachet 32 may be defined by a breathable material, for example, a material substantially similar to that described with reference to breathable membrane 22. In particular, moisture and oxygen may be permeable into sachet 32 so that moisture oxygen scavenging composition 34 may adsorb, absorb, chemisorb, react with, or otherwise substantially retain oxygen and moisture within sachet 32 to divert oxygen and moisture from package 10, 10a, or 10b. For example, sachet 32 may be a moisture- and gas-permeable sachet including moisture oxygen scavenging composition 34. In some examples, a major surface 24a defined by sachet 32 may carry an adhesive layer 26a. Adhesive layer 26a may be substantially similar in geometry and composition to adhesive layer 26. In some examples, sachet 32 may carry adhesive layer 26 only in peripheral region 25 of major surface 24a, as shown in FIG. 4B.

Figure 4C:
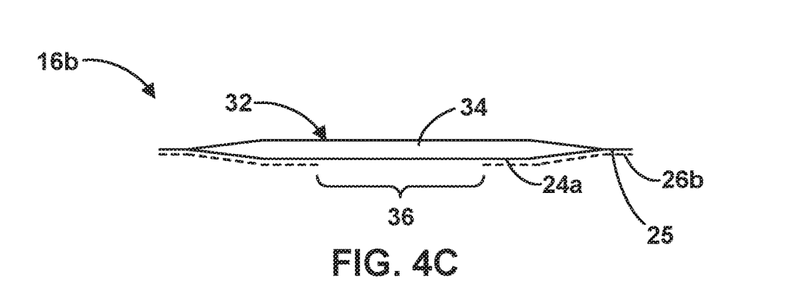
FIG. 4C is a conceptual diagram illustrating a side view of a moisture oxygen scavenger including a sachet, with an adhesive layer applied to a peripheral surface region of the sachet and a region inward of the peripheral surface region.

FIG. 4C is a conceptual diagram illustrating a side view of a moisture oxygen scavenger 16b including sachet 32, with an adhesive layer 26b applied to peripheral surface region 25 of sachet 32 and a region inward of peripheral surface region 25. As shown in FIG. 4C, adhesive layer 26b may be substantially absent in an interior region 36 defined by sachet 32. Adhesive layer 26b may otherwise be substantially similar in geometry and composition to adhesive layer 26. Interior region 36 may be adjacent window 18, and substantially conforms to the contour of window 18, or of breathable membrane 22.

Figure 4D:
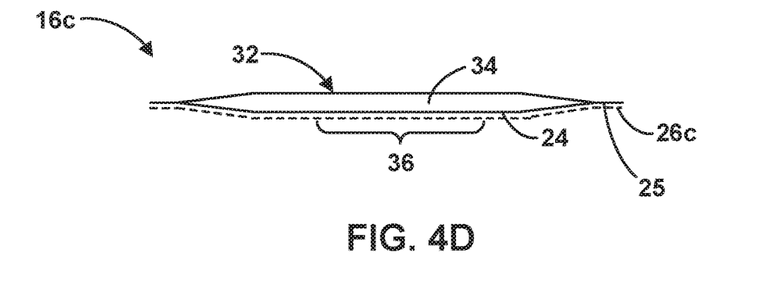
FIG. 4D is a conceptual diagram illustrating a side view of a moisture oxygen scavenger including a sachet, with an adhesive layer applied substantially across an entire major surface of the sachet.

FIG. 4D is a conceptual diagram illustrating a side view of a moisture oxygen scavenger 16c including sachet 32, with an adhesive layer 26c applied substantially across entire major surface 24 of the sachet. Thus, adhesive layer 26c extends across both peripheral surface region 25 and interior region 36. Adhesive layer 26c may otherwise be substantially similar in geometry and composition to adhesive layer 26. In some examples, adhesive layer 26c may exhibit different adhesive patterns in peripheral surface region 25 and interior region 36. For example, adhesive layer 26c adjacent peripheral surface region 25 may be continuous, while adhesive layer 26c adjacent interior region 36 may be discontinuous, or vice versa. Adhesive layer 26c may exhibit different adhesive strengths across major surface 24a, for example, being weaker adjacent peripheral surface region 25, and stronger adjacent interior region 36, or vice versa.

Thus, in example packages according to the disclosure, a moisture oxygen scavenger may be adhered to a package body adjacent a window and a breathable membrane, to reduce or prevent exposure of moisture or oxygen in an interior of the package body or to a medical supply housed in the package body.

Figure 5:
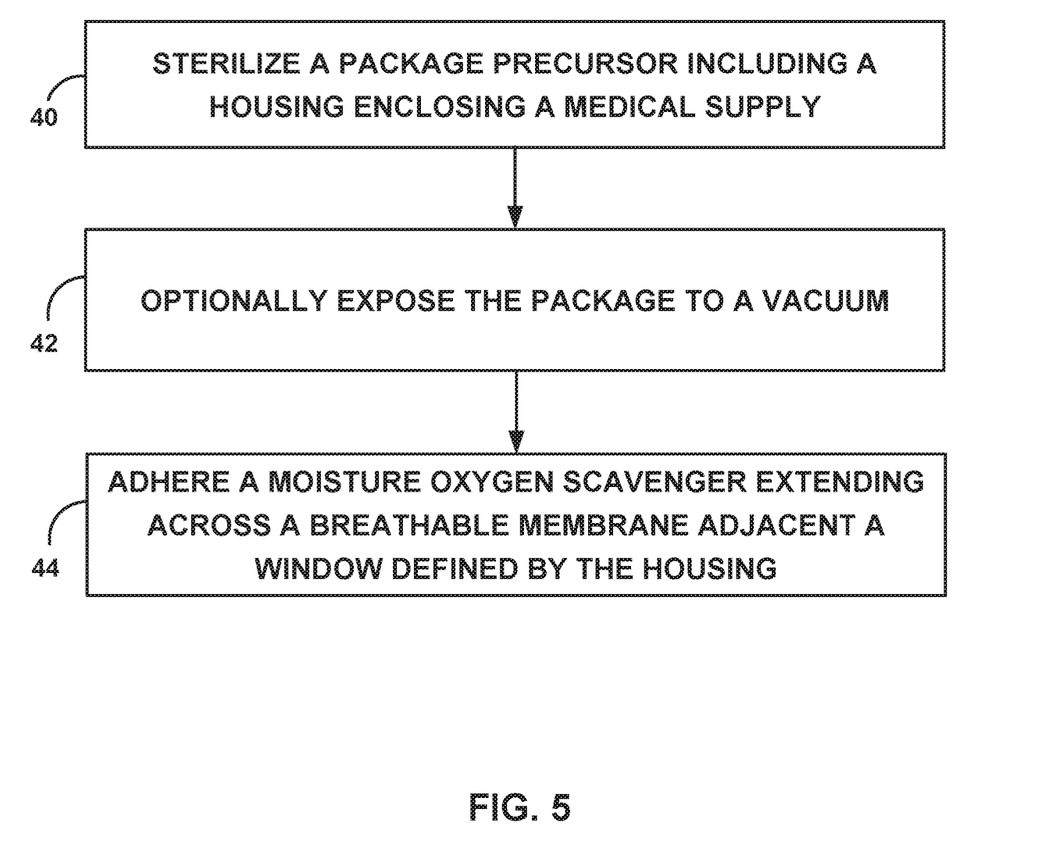
FIG. 5 is a flow diagram illustrating an example technique for forming a package including a package body enclosing a medical supply and a moisture oxygen scavenger extending across a breathable membrane adjacent a window defined by the package body.

FIG. 5 is a flow diagram illustrating an example technique for forming a package (10, 10a, 10b) including package body 12 enclosing medical supply 14 and a moisture oxygen scavenger (16, 16a, 16b, 16c) extending across breathable membrane 22 adjacent window 18 defined by package body 12. While the example technique of FIG. 5 is described with reference to example packages 10, 10a, and 10b described with reference to FIGS. 1A, 1B, 2, and 3, the example technique of FIG. 5 may be used to prepare any example articles according to the disclosure.

The technique includes sterilizing a package precursor (40). The package precursor includes package body 12 enclosing medical supply 14 within the internal volume of package body 12. In some examples, the technique optionally includes forming the package precursor by introducing medical supply 14 into the internal volume of package body 12 through an opening defined by package body 12, and sealing the opening to form seal 15. Sterilizing the package precursor (40) includes exposing the package precursor to a sterilizing agent. In some examples, the sterilizing agent includes ethylene oxide. For example, package body 12 may be introduced in a volume of ethylene oxide or in a flow of ethylene oxide for a predetermined period of time. In some examples, sterilizing the package precursor (40) may include, in addition to exposure to a sterilizing agent, exposure to ultraviolet (UV) radiation, microwave treatment, high-pressure treatment, or any other sterilization technique.

In some examples, the technique of FIG. 5 optionally includes, after sterilizing the package precursor (40), exposing package body 12 to a vacuum (42). For example, package body 12 may be introduced into a vacuum chamber, or vacuum may be applied to an enclosed region in which package body 12 is maintained. In some examples, only an internal volume of package body 12 may be exposed to a vacuum, for example, by disposing a vacuum hose sealed about or otherwise adjacent window 18, and pulling air or gas out of the internal volume of package body 12 through window 18. Exposing package body 12 to a vacuum (42) may cause residual sterilizing agent, for example, residual ethylene oxide, to be removed from the internal volume of package body 12 or medical supply 14. In some examples, exposing package body 12 to a vacuum (42) may also cause one or both of moisture or oxygen to be removed from the internal volume of package body 12 or medical supply 14.

After sterilizing the package precursor (40), and after optionally exposing package body 12 to a vacuum (42), the technique of FIG. 5 includes adhering moisture oxygen scavenger 16, 16a, 16b, or 16c to package body 12 (44). For example, adhesive layer 26, 26a, 26b, 26c may be pre-applied to moisture oxygen scavenger 16, 16a, 16b, or 16c, and moisture oxygen scavenger 16, 16a, 16b, or 16c may be pressed against package body 12 to cause moisture oxygen scavenger 16, 16a, 16b, or 16c to be secured to package body 12. In some examples, adhering moisture oxygen scavenger 16, 16a, 16b, or 16c to package body 12 (44) may include applying adhesive layer 26, 26a, 26b, 26c to one or both of moisture oxygen scavenger 16, 16a, 16b, or 16c or package body 12. Adhering moisture oxygen scavenger 16, 16a, 16b, or 16c to package body 12 (44) may include using a brush, a pull-down applicator, spraying, or any suitable technique for applying adhesive layer 26, 26a, 26b, 26c in a predetermined pattern. Thus, adhering moisture oxygen scavenger 16, 16a, 16b, or 16c to package body 12 (44) ultimately includes applying adhesive layer 26, 26a, 26b, 26c between moisture oxygen scavenger 16, 16a, 16b, 16c, and package body 12. In some examples in which package body 12 is exposed to a vacuum (42), adhering moisture oxygen scavenger 16, 16a, 16b, or 16c to package body 12 (44) may also be performed in a vacuum. In some examples in which package body 12 is exposed to a vacuum (42), adhering moisture oxygen scavenger 16, 16a, 16b, or 16c to package body 12 (44) may be performed substantially immediately after exposing package body 12 to the vacuum (42), for example, with a sufficiently low intervening time interval to reduce or prevent migration or transmission of moisture or air or other contaminants to package 12.

In some examples, adhering moisture oxygen scavenger 16, 16a, 16b, or 16c to package body 12 (44) may include aligning backing layer 30 with moisture oxygen scavenger 16, 16a, 16b, 16c, so that moisture oxygen scavenger 16, 16a, 16b, 16c is between backing layer 30 and package body 12. Adhering moisture oxygen scavenger 16, 16a, 16b, or 16c to package body 12 (44) may include pressing backing layer 30 against package body 12, so that an adhesive layer (for example, the second adhesive layer) is carried on major surface 31 defined by backing layer 30 and between package body 12 and moisture oxygen scavenger 16, 16a, 16b, 16c. In some examples, adhering moisture oxygen scavenger 16, 16a, 16b, or 16c to package body 12 (44) only includes applying adhesive to major surface 31, and adhesive layer 26, 26a, 26b, 26c may not be applied between moisture oxygen scavenger 16, 16a, 16b, 16c, and package body 12.

Thus, example techniques according to the disclosure may be used to form packages for housing or enclosing medical supplies including moisture oxygen scavengers.

Various examples have been described. These and other examples are within the scope of the following claims.

The invention claimed is:

1. A package comprising:
    a package body enclosing a medical supply, wherein the package body defines a window;
    a breathable membrane adjacent the package body and extending across the window;
    a moisture oxygen scavenger adjacent the package body and extending across an outer surface of the breathable membrane; and
    and adhesive layer, wherein the adhesive layer is configured to hold the moisture oxygen scavenger adjacent the breathable membrane.

2. The package of claim 1, wherein the adhesive layer contacts a major surface defined by the moisture oxygen scavenger, and wherein the adhesive layer is between the package body and the moisture oxygen scavenger.

3. The package of claim 1, wherein the adhesive layer substantially surrounds the window.

4. The package of claim 3, wherein the adhesive layer is absent in a region extending across the window.

5. The package of claim 3, wherein the adhesive layer extends across the window.

6. The package of claim 1, further comprising a backing layer adjacent the package body, wherein the backing layer extends across the moisture oxygen scavenger, wherein the moisture oxygen scavenger is between the backing layer and the package body.

7. The package of claim 6, wherein the adhesive layer contacts a major surface defined by the backing layer, and wherein the adhesive layer is between the backing layer and the package body.

8. The package of claim 7, wherein the adhesive layer substantially surrounds the moisture oxygen scavenger.

9. The package of claim 8, wherein the adhesive layer is absent in a region extending across the moisture oxygen scavenger.

10. The package of claim 8, wherein the adhesive layer extends across the moisture oxygen scavenger.

11. The package of claim 6, wherein the backing layer defines a product label.

12. The package of claim 1, wherein the breathable membrane is gas- and moisture-permeable and microorganism- and liquid-impermeable.

13. The package of claim 1, wherein the moisture oxygen scavenger comprises a moisture- and gas-permeable sachet comprising a moisture oxygen scavenging composition.

14. The package of claim 1, wherein the moisture oxygen scavenger comprises a carrier layer and a moisture oxygen scavenging composition in contact with a major surface defined by the carrier layer, wherein the moisture oxygen scavenging composition is between the carrier layer and the package body.

15. The package of claim 1, wherein the package comprises a first package body portion and a second package body portion, wherein the package body is defined by the first and second package body portions.

16. The package of claim 1, wherein the package comprises one or more of a woven panel, a non-woven panel, a plastic panel, a polymer film, a paper film, a coated paper film, a metalized polymer film, a foil, a tray, a thermoform, a two-piece clamshell, or a folded clamshell.

17. The package of claim 1, wherein the moisture oxygen scavenger comprises a moisture vapor transmission rate sufficiently low to prevent exposure of the medical supply to moisture or oxygen beyond a respective predetermined threshold.

18. The package of claim 6, wherein the backing layer is porous.

* * * * *